US00PP29981P2

(12) United States Plant Patent
Delabroye

(10) Patent No.: US PP29,981 P2
(45) Date of Patent: Dec. 11, 2018

(54) ***HEUCHERA* PLANT NAMED 'ORANGE DREAM'**

(50) Latin Name: ***Heuchera* hybrid**
Varietal Denomination: Orange Dream

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 15/530,411

(22) Filed: Jan. 10, 2017

(51) Int. Cl.
*A01H 5/12* (2018.01)

(52) U.S. Cl.
USPC ..... Plt./440

(58) Field of Classification Search
USPC ..... Plt./440
CPC ... A01H 5/12; A01H 5/02; A01H 5/00; A01H 5/025; A01H 6/80
See application file for complete search history.

(56) References Cited

PUBLICATIONS

GP Plants Saleslist for spring 2016 (Dec. 8, 2015) retrieved on Feb. 14, 2018, retrieved from the Internet at www.gpplants.com/wp-content/uploads/Sales-List-2016-12-08-20151.xls, 2 pp. (Year: 2015).*

* cited by examiner

*Primary Examiner* — June Hwu
(74) *Attorney, Agent, or Firm* — Penny J. Aguirre

(57) ABSTRACT

A new cultivar of *Heuchera* named 'Orange Dream' that is characterized by its compact plant habit, its leaves that are orange in color and its flowers that are white in color.

2 Drawing Sheets

Botanical classification: *Heuchera* hybrid.
Cultivar designation: 'Orange Dream'.

BACKGROUND OF THE INVENTION

The present invention relates to a new and distinct cultivar of *Heuchera* of hybrid origin, botanically known as a *Heuchera* and is hereinafter referred to by its cultivar name 'Orange Dream'.

The new cultivar was discovered as a chance seedling in a trial field by the Inventor in Hantay, France in May of 2014. The trial field contained hundreds of proprietary *Heuchera* seedlings from the Inventor's breeding program. The exact parentage of 'Orange Dream' is therefore unknown.

Asexual propagation of the new cultivar was first accomplished under the direction of the Inventor by in vitro propagation initiated from meristem tissue in Rijswijk, The Netherlands in June 2015. Asexual propagation of the new cultivar by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Orange Dream' as a new and unique cultivar of *Heuchera*.

1. 'Orange Dream' exhibits a compact plant habit.
2. 'Orange Dream' exhibits leaves that are orange in color.
3. 'Orange Dream' exhibits flowers that are white in color.

'Orange Dream' can be most closely compared to the *Heuchera* cultivars 'Vulcano' (U.S. Plant Pat. No. 25,625) and 'Apricot' (U.S. Plant Pat. No. 27,139). Both are similar to 'Orange Dream' in having orange toned foliage. 'Vulcano' is also similar to 'Orange Dream' in foliage shape. 'Vulcano' differs from 'Orange Dream' in having leaves that are deeper orange in color. 'Apricot' differs from 'Orange Dream' in having leaf surfaces that are glossier, leaf-lobes that are round in shape, more numerous flowering stems, and flowers that are pink in color.

BRIEF DESCRIPTION OF THE DRAWINGS

The accompanying colored photograph illustrates the overall appearance and distinct characteristics of the new *Heuchera*. The photograph was taken of a plant one year in age as grown in a greenhouse in a 27-cm container in Hantay, France.

The photograph in FIG. 1 provides a side view of the plant of 'Orange Dream' in bloom.

Figure 1:
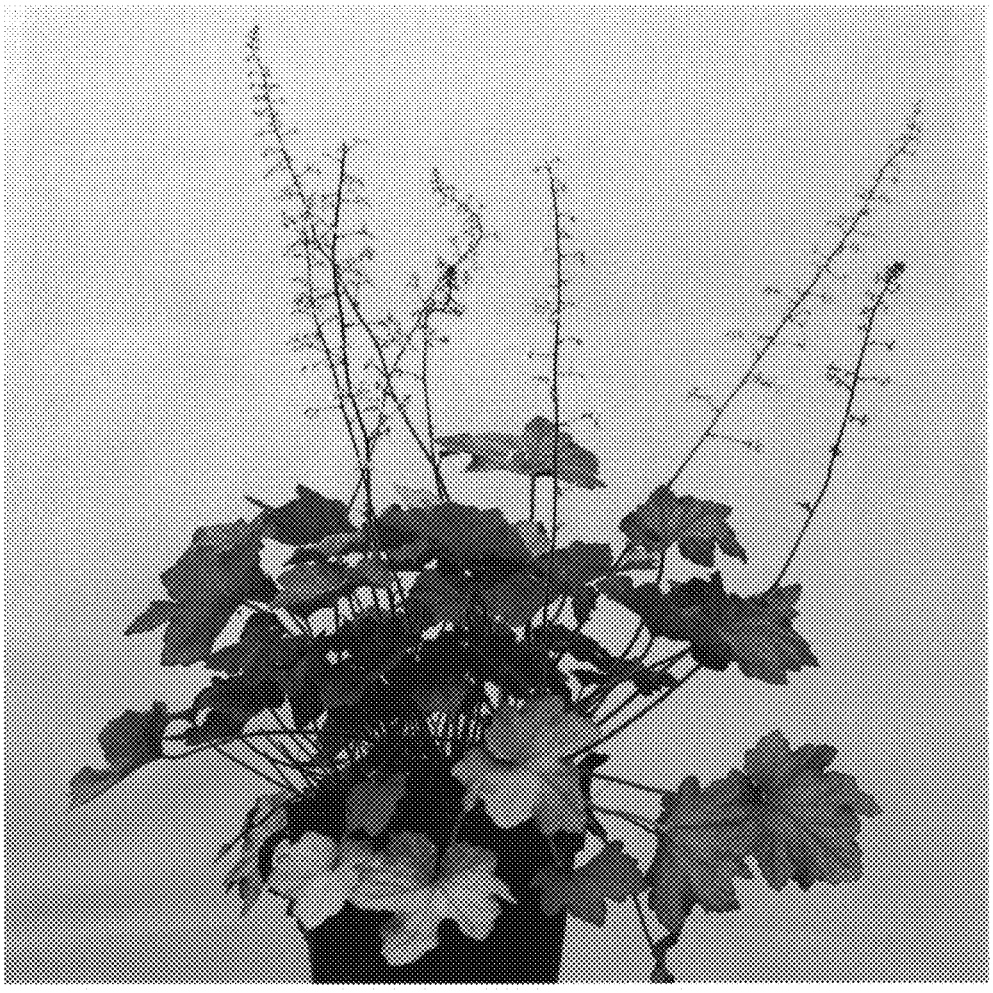
Figure 2:
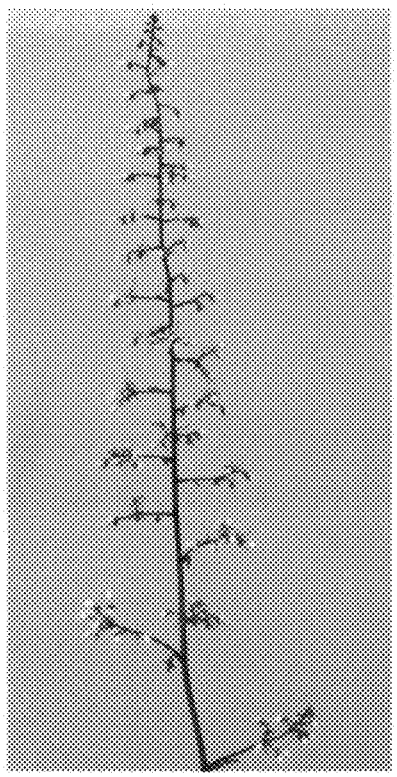

The photograph in FIG. 2 provides a close up of the inflorescence of 'Orange Dream'.

Figure 3:
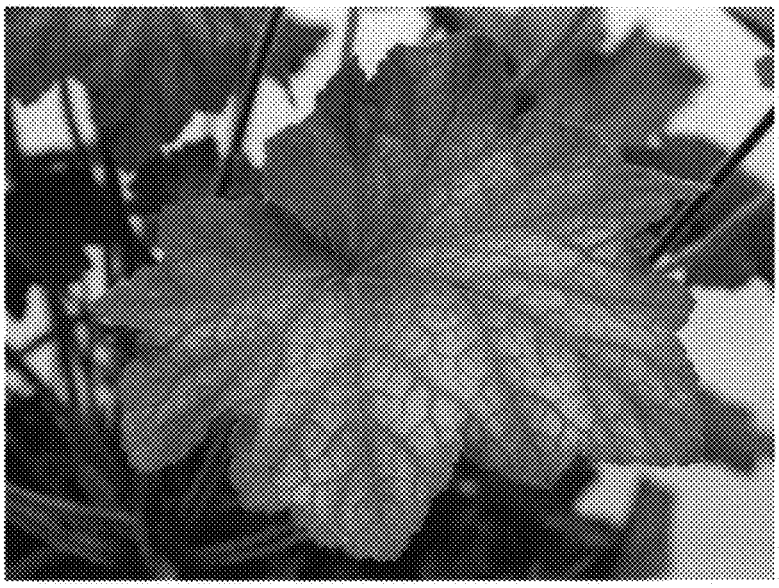

The photograph in FIG. 3 provides a close up of the foliage of 'Orange Dream'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 27-cm containers in Hantay, France. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Long blooming; an average of 6 weeks from May into June in The Netherlands.

*Plant type*.—Herbaceous perennial.

*Plant habit*.—Compact and open-mounded.

*Height and spread*.—An average of 42 cm in height to top of foliage (83 cm to top of inflorescence) and 73 cm in width as a one year-old plant.

*Hardiness*.—At least in U.S.D.A. Zones 3 to 9.

*Diseases and pests*.—Not unique susceptibility/resistance to pests or diseases has been observed.

*Root description*.—Fibrous roots on woody rootstalks, 158D in color.

*Propagation*.—Tissue culture.

*Root development*.—An average of 13 weeks to fully develop from a tissue culture plug in a 7-cm or larger container.

*Growth rate*.—Moderate.

Stem description (peduncle, flowering stem):

*Shape*.—Round.

*Stem color*.—178A.

*Stem size*.—Primary peduncle; an average of 3 mm in diameter and 70.9 cm in length, secondary peduncle; an average of 1.5 mm in diameter and 1.5 cm in length.

*Stem strength*.—Strong.

*Stem aspect*.—Flowering stems grow at an angle of 90° to 45° (0°=horizontal).

*Stem surface*.—Densely covered with short soft glandular hairs; an average of 1.5 mm in length and 183B to 183D in color.

*Stem number*.—Average of 8 flowering stems.

*Internode*.—An average of 2 mm in length.

*Branching habit*.—Flowering stems emerge from basal rosette.

Foliage description:

*Leaf shape*.—Orbicular.

*Leaf division*.—Simple.

*Leaf base*.—Hastate, touching to slightly overlapping.

*Leaf apex*.—Short abruptly acute.

*Leaf venation*.—Laciniate, upper surface 174B, lower surface 182D.

*Leaf margins*.—A average of 6 ovate-shaped lobes with lobe margins crenate with abruptly acute tips on each tooth.

*Leaf attachment*.—Petiolate.

*Leaf arrangement*.—Alternate in basal rosettes.

*Leaf lobes*.—Lobed, an average of 7 lobes, shallow in depth, divergent.

*Leaf orientation*.—Typically nearly horizontal to petiole and slightly cupped.

*Leaf surface*.—Upper surface and lower surface is dull and pubescent, upper surface is moderately covered with very short hairs an average of 0.5 mm in length and 186D in color, lower surface is densely covered with short hairs an average of 1 mm in length and between 156D and 186D in color.

*Leaf color*.—Young upper and lower surface is 185B, mature upper surface a color between 164A and 165A with 159A between veins and fading to 182D when fully mature with edges 166B, mature surface 185C, fall coloration both surface similar to mature coloration, winter color similar to fully mature coloration but suffused with 166B.

*Leaf size*.—An average of 15.4 cm in length and 15.1 cm in width.

*Leaf quantity*.—An average of 16 per basal rosette.

*Petioles*.—An average of 24.6 cm in length and 3.5 mm in diameter, upper and lower surface color is 183B, both surfaces are glossy, moderate in strength, densely covered with soft hairs an average of 1.75 mm in length and between 156D and 186D in color.

*Stipules*.—Small leafy stipules at the base of each leaf, acute apex, an average of 1.5 cm in length and 3 mm in width, N77B in color.

Flower description:

*Inflorescence type*.—Numerous small bell-shaped flowers arranged on panicles on peduncles emerging from a basal rosette.

*Inflorescence size*.—An average of 34 cm in height and 9.9 cm in diameter.

*Inflorescence number*.—An average of 8.

*Flower fragrance*.—None.

*Flower quantity*.—Average of 400 flowers per flowering stem.

*Flower lastingness*.—Average of one week.

*Flower buds*.—Obovate in shape, an average of 1.5 mm in diameter and 3 mm in diameter, upper half is N155C, base is 186C, dull surface densely covered with very short glandular hairs; an average of 0.5 mm in length and too small to measure color.

*Flower aspect*.—Upright, outwardly and nodding.

*Flower type*.—Single, campanulate.

*Flower size*.—About 3.5 mm in length and 6.5 mm in diameter.

*Petals*.—About 5, rotate arrangement and implanted in the hypanthium at base, oblanceolate in shape, margin is entire, apex is acute, upper and lower surface is glabrous and smooth, color of upper and lower surface when opening and when fully open; NN155D, an average of 2 mm in length and 0.5 mm in width.

*Calyx*.—Campanulate, sepals fused to hypanthium, 4 mm in length and 2.5 mm in diameter.

*Sepals*.—An average of 5, lower 62.5% fused into campanulate hypanthium, short oblong in shape, an average of 4 mm in length and 1 mm in width, margin is entire and fused into hypanthium, apex is obtuse, fused base, color; when opening upper and lower surface 158D with base 186C to 186D, fully open upper and lower surface NN155B with base 186D, both surfaces are dull, lower surface is moderately covered with very short glandular hairs an average of 0.2 mm in length and to small to measure color.

*Pedicels*.—An average of 2 mm in length and 0.5 mm in diameter, primary flower aspect straight on top of secondary pedicel, secondary and tertiary flower aspect is 45°, moderate in strength, surface dull and densely covered with very short soft glandular hairs; average of 0.2 mm in length and to small to measure color, 174D in color and fading to 152D.

Reproductive organs:

*Gynoecium*.—Pistils; 2, 4 mm in length, stigma; club-shaped, N155B in color, 0.2 mm in diameter, style; an average of 3.75 mm in length and NN155D in color, fading towards the ovary becoming 150D, ovary; 150D in color.

*Androecium*.—Stamens; 5, anthers; triangular in shape, about 0.3 mm in length and 24A to 24B in color, filament; 3.5 mm in length and NN155D in color, pollen; low to moderate in quantity and 23A in color.

*Seed/fruit*.—No fruit or seeds were observed to date.

It is claimed:

1. A new and distinct cultivar of *Heuchera* plant named 'Orange Dream' as herein illustrated and described.

* * * * *